United States Patent [19]

Whitehead

[11] 4,399,812
[45] Aug. 23, 1983

[54] PENILE PROSTHETIC DEVICE

[76] Inventor: Edgar D. Whitehead, 785 Park Ave., New York, N.Y. 10021

[21] Appl. No.: 336,166

[22] Filed: Dec. 31, 1981

[51] Int. Cl.³ .............................................. A61F 5/00
[52] U.S. Cl. ............................................... 128/79; 3/1
[58] Field of Search .................................. 128/79; 3/1

[56] References Cited

U.S. PATENT DOCUMENTS

| | | | |
|---|---|---|---|
| 3,853,122 | 12/1974 | Strauch et al. | 128/79 |
| 3,893,456 | 7/1975 | Small et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,224,934 | 9/1980 | Scott et al. | 128/79 |
| 4,235,227 | 11/1980 | Yamanaka | 128/79 |
| 4,267,829 | 5/1981 | Burton et al. | 128/79 |
| 4,353,360 | 10/1982 | Finney et al. | 128/79 |

*Primary Examiner*—Stephen C. Pellegrino
*Attorney, Agent, or Firm*—Charles E. Baxley

[57] ABSTRACT

Typical embodiments of the invention overcome male sexual dysfunction or impotence. Illustratively, a prosthetic device for implantation within the penis has a pumping mechanism that is integral with and in fluid communication with a fluid storage section. Fluid is pumped manually from storage to a distal expansile section that inflates to render the penis rigid and capable of sexual activity. Undesirable distention of the penis is avoided through a pressure relief valve that permits fluid to flow from the expansile section back into the storage section if the pressure in the expansile section becomes too great.

3 Claims, 3 Drawing Figures

PENILE PROSTHETIC DEVICE

This invention relates to prosthetic apparatuses and methods, and more specifically to a prosthetic device for implantation within a penis in which a quantity of fluid is shifted within the device to produce selectively erect and flaccid penis conditions.

A number of prosthetic devices have been proposed for implantation within a penis, but each of these devices has limitations. Illustratively, the Small-Carrion prosthesis, the Finney prosthesis and the Jonas prosthesis require implantation of a pair of rods within the body of the penis. The Small-Carrion rods are quite rigid, often requiring use of restrictive clothing because of the permanent state of erection that is produced. The Finney and Jonas devices, however, do permit flexibility that enables the penis to be "dressed", that is, to assume a dependent position. All of these prosthetic devices nevertheless fail to increase the girth or turgor of the penis. The prosthetic devices themselves also might create a degree of urethal resistance that prevents subsequent endoscopic urologic investigation or treatment. The Finney and Jonas prostheses moreover have been known to buckle during coition.

The Scott prosthesis enables the penis to change from a flaccid state to a rigid state through a system that transfers hydraulic fluid from a reservoir in the abdomen to inflatable cylinders within the penis. Thus the Scott prosthesis imparts to the penis a normal selectively flaccid or erect appearance (including, during erection, normal increases in girth and in length). Although the Scott prosthesis overcomes a number of undesirable features of the Small-Carrion, Finney and Jonas devices, it is nevertheless unsatisfactory for several reasons. The Scott prosthesis is mechanically complicated and involves several components including inflatable penile cylinders, a scrotally located pumping device, an abdominally located fluid reservoir and associated tubing and connectors. Consequently the Scott apparatus is subject to mechanical failure and must be implanted through a relatively long and exacting surgical procedure.

In these circumstances there is a need for a selectively inflatable prosthesis that is mechanically simple and reliable and that also involves a relatively straightforward implantation surgical procedure which does not require special surgical instruments or skills, lengthy periods of hospitalization or great expense to the patient.

These objectives are attained through the practice of the present invention. Illustratively, within a unitary prosthetic device, a fluid storage section is in fluid communication through a finger pressure operated pumping mechanism with a distal expansile section. This prosthesis can be either a parallel double type, in which two independent and complete fluid transfer units are provided one in each of two parallel devices, to deal with congenital or acquired asymmetry of the corpora cavernosa; or a single conjoined type, for normal symmetrical corpora cavernosa, with one pumping mechanism and one fluid storage section.

In the parallel double prosthesis, the individual devices each are inserted through small respective incisions in the fibrous covering of the penis or tunica albuginea. In this way each device is implanted in one of the two bodies of erectile tissue or corpus cavernosa that lie side-by-side to form the larger protruberant part of the penis.

The single conjoined prosthesis, however, is placed in both corpora cavernosa through an incision in the tunica albuginea and by means of a division of the membrane partition that separates the two corpora cavernosa, the intercrural septum. The two diverging tails of this single conjoined prosthesis are placed in separate portions of the posterior part under the pubic arch, which is technically referred to as the ischial cavernosa or crura.

In either prosthetic device, the penis is made rigid through a sequence of manual compressions of the pumping mechanism. This manipulation draws fluid from one or more of the storage sections and transfers this fluid to a distal expansion section in order to inflate the volume between the expansible section and an outer membrane; thereby increasing the girth, length and rigidity of the penis.

Because the parallel double prosthesis has two separate devices, each equipped with its own pumping mechanism, manipulation of only one pump provides for differential inflation of the penis on only one side of the intercrural septum. Should it be desired to inflate the other side of the penis, it will be necessary with the parallel double prosthesis, to manipulate the pumping mechanism in the other device.

To prevent over distension of the penis through pumping the fluid to too high a pressure as the penis is made rigid, a valve between the fluid storage section and the distal expansile section permits the fluid to flow back into the storage section, if the fluid pressure in the distal expansile section reaches a predetermined level.

The invention will be appreciated more completely through a study of the following detailed description of preferred embodiments of the invention. The scope of the invention, however, is limited only through the claims appended hereto.

FIG. 3 is a side elevation in full section of the prothesis shown in FIG. 2, taken along the line A—A of FIG. 2 and viewed in the direction of the arrows.

Figure 1:
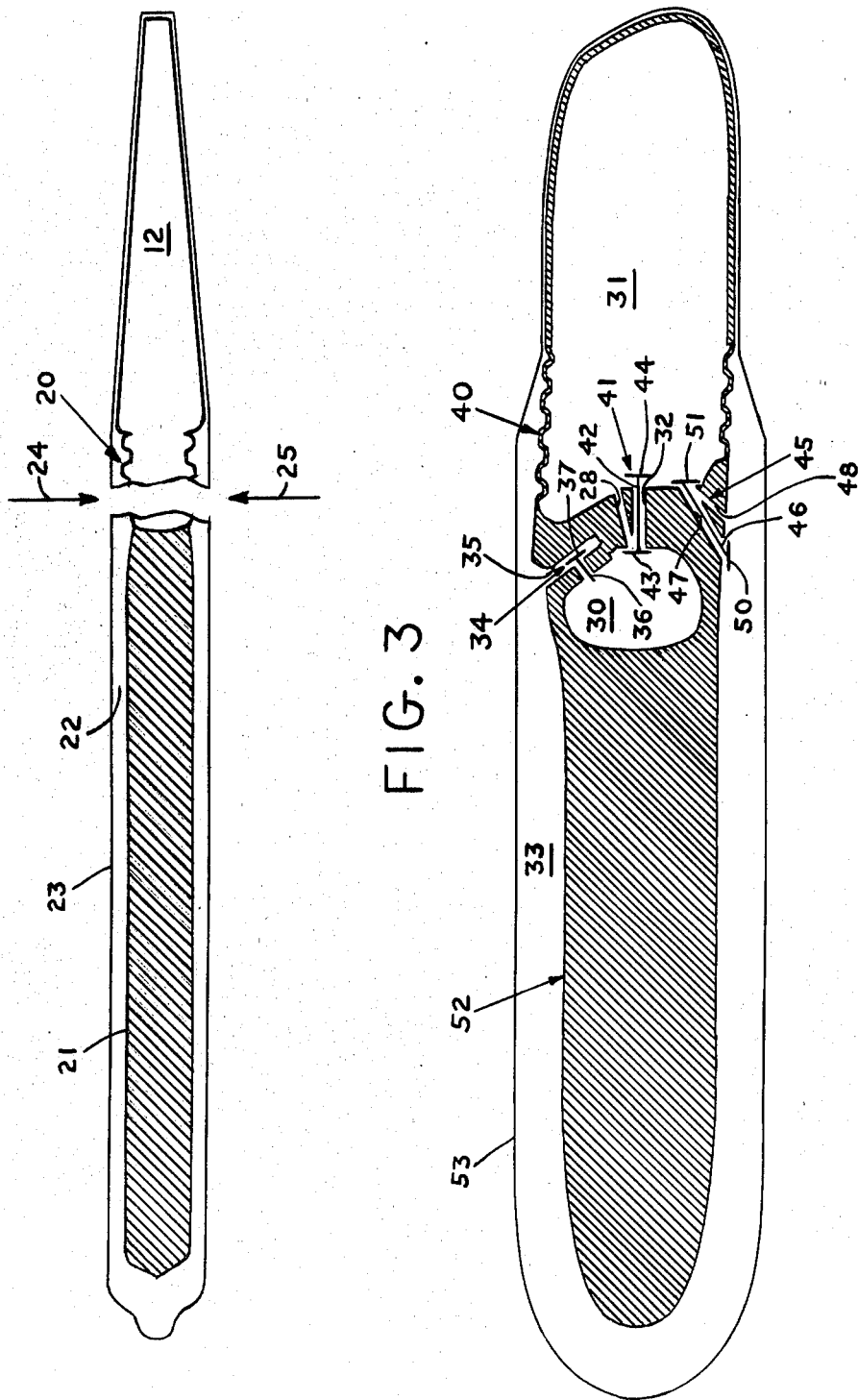
FIG. 1 is a plan view in full section of one embodiment of a device for a typical parallel double prosthesis that illustrates principles of the invention.

The prosthesis shown in FIG. 1 is made of suitably flexible material to which the human body is tolerant, of which one or more of the silicone elastomers are typical.

Attention is invited to FIG. 1 which shows one of the two devices required for the parallel double prosthesis embodiment of the invention. As illustrated, an individual pumping mechanism 30 is in fluid communication with a pressurized fluid storage section 31 by way of a conduit 32. Fluid communication is selectively established with a distal expansile section 33 through a check valve 34 and a passageway 35. The check valve 34 comprises a valve stem 36 that is received for longitudinal sliding movement within the fluid duct that joins the interior volume of the pumping mechanism 30 with the passageway 35. A valve seat 37 is connected to the end of the valve stem 36 that protrudes into the passageway 35.

In these circumstances, when the check valve 34 is closed to block fluid communication between the pumping mechanism 30 and the passageway 35, the valve seat 37 is pressed against the side of the passageway 35 in which the check valve 34 is mounted. With the check valve 34 open, however, the valve seat abuts the opposite side of the passageway 35. In this manner, the walls of the passageway 35 limit the movement of the valve seat 37 and retain the valve stem 36 within the fluid duct.

The fluid storage section 31 is an elongated, fluid filled bladder that is connected to the wall of the passageway 35 opposite to the pumping mechanism 30 and to a portion of the housing for the pumping mechanism by means of a bellows 40.

Fluid communication also is established from the fluid storage section 31 to the interior of the pumping mechanism 30 by way of a one-way check valve 41 in the conduit 32 and an angularly disposed side channel 28. As shown, the check valve 41 has a valve stem 42 that is somewhat longer than the conduit 32. Within the interior of the pumping mechanism 30 the valve stem 42 terminates in a valve seat 43 that, when pressed against the orifice of the conduits 28 and 32, blocks these passageways and prevents fluid from flowing from the pumping mechanism to the fluid storage section. Within the fluid storage section 31, that protruding portion of the valve stem 41 terminates in a transversely disposed stop 44, the diameter of the stop being appreciably greater than the diameter of the inlet to the conduit 32 but less than the inlet to the conduit 28. Thus, when the check valve 41 is open to permit fluid to flow into the pumping mechanism from the storage section 31, the stop nevertheless retains the valve stem 42 within the conduit 32 but enables fluid to flow from the reservoir 31 into the pumping mechanism 30 by way of the angularly disposed channel 28.

The fluid storage section 31 also is equipped with a pressure relief valve 45 that permits fluid to flow from the distal expansile section 33 back into the fluid storage section if the pressure in the expansile section becomes higher than some predetermined limit of safety for the distention of the surrounding penis. Illustratively, this predetermined limit is produced by testing the patient before implantation. A tourniquet is applied to the base of the penis and a saline solution is injected into the penis to determine the pressure and volume that is required to satisfy the cosmetic and physical needs of a particular patient. In this way the volume of fluid and the pressure within the reservoir 31 of the device described herein is determined on a patient-by-patient basis.

The pressure relief valve 45 also is a one way flow check valve in which a valve stem 46 is received within a slightly shorter conduit 47. Note also that another conduit 48, angularly oriented relative to the conduit 47 also establishes fluid communication between the reservoir 31 and the expansile section 33. The end of the valve stem 46 that protrudes into the expansile section 33 terminates in a stop 50 that is angularly disposed relative to the conduit 47. This limits the longitudinal depth of travel of the stem through the conduit 47 toward the interior of the storage section 31. Within the fluid storage section 31 the valve stem 46 terminates in a valve seat 51 that, when pressed by fluid pressure within the storage section against the orifices of the conduits 47 and 48, block fluid flow from the storage section 31 into the expansile section 33. When open, however, through a predetermined higher fluid pressure within the expansile section 33, the valve seat 51 is unseated and permits flow from the expansible section into the storage section.

The distal end of the pumping mechanism 30 is connected to a soft but solid extension 52. The extension 52 permits a flaccid dependent penis when the expansile section 33 is not under a charged pressurized state.

The outer surface of the soft, but solid extension 52 forms the inner surface that defines the distal expansile section 33. A flexible membrane 53 is joined on the proximal end to the outer surface of the bladder that forms a fluid storage section 31, the balance of the membrane enclosing the pumping mechanism 30 and the extension 52 to provide the outer elastic surface for the distal expansile section 33.

In operation, an incision is made in the proximal end of the tunica albuginea and the device shown in FIG. 1 is implanted lengthwise on one side of the intercrural septum in one of the two corpora cavernosa. A second device is implanted through another proximal incision in the other corpus cavernosa. In both instances the respective fluid storage sections 31 are surgically lodged in separate ischial cavernosa, under the pubic arch. The expansile sections 33, however, terminate distal to the corona of the glans penis.

In FIG. 1, in order to render one side of a penis rigid, the pumping mechanism 30 is pressed between thumb and index finger in order to close the check valve 41 and to express fluid from the interior of the pumping mechanism through the opened check valve 34 and its associated conduit 35 into the distal expansile section 33. Upon releasing the finger pressure, the check valve 34 closes and the relatively lower pressure within the pumping mechanism 30 causes the check valve 41 to close and permit fluid to flow from the storage section 31 into the pumping mechanism 30 by way of the still open conduit 28. To accommodate for fluid transferred from the storage section 31 in the foregoing manner, the bellows 40 contracts and the membrane 53 expands to increase the rigidity on one side of the penis. Successive manipulations of the pumping mechanism should bring the side of the penis in question into a satisfactory state of rigidity. Should too much pumping produce an undesirable distention of the penis, the relatively higher fluid pressure in the expansile section 33 will force the pressure relief valve 45 open to permit excess fluid to flow into the fluid storage section 31. In this way, the pressure is relieved in the expansile section 33 and the distention of the penis is reduced to an acceptable level without regard to the number of times the pumping mechanism 30 may be activated.

It will be recalled that a companion to the device shown in FIG. 1 is lodged in the other corpus cavernosa on the other side of the intercrural septum. This parallel, companion device also may be inflated in the manner described above to produce a satisfactory degree of rigidity in the other side of the penis, thereby preparing the penis for satisfactory sexual activity. Upon completion of sexual activity, gentle manual pressure on the penis will increase the fluid pressure in the distal expansile section. This increased pressure will cause the pressure relief valve 45 to open while nevertheless closing the stop 50 and its associated passageway 47. Flow into the reservoir is achieved, however, through the still open conduit 48 and thus permitting the fluid to flow back into the storage section 31, the bellows 40 expanding to compensate for the increased volume of fluid within the storage section 31.

Figure 2:
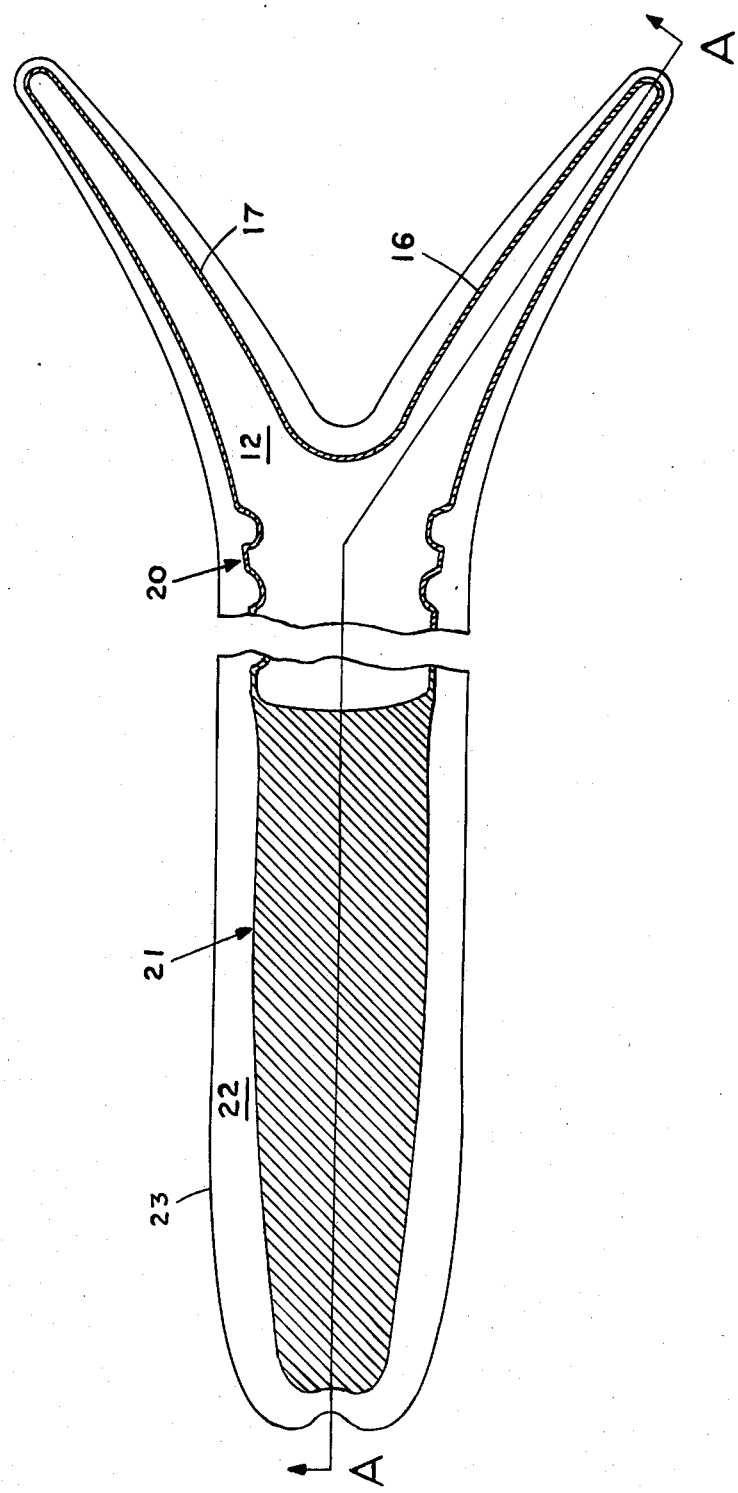
FIG. 2 is a plan view in full section of a typical conjoined single prosthesis illustrating principles of the invention.

Attention now is invited to FIGS. 2 and 3 which illustrate a conjoined single prosthesis that embodies salient features of the invention. More specifically, a pumping mechanism similar to that described in connection with the device shown in FIG. 1 is in fluid communication with fluid storage section 12 that has been pressurized to a level determined in the manner previously described. As the pumping mechanism is successively squeezed between thumb and index fingers as previously mentioned, the pressure in the prosthesis cannot ever exceed a pressure higher than a safe, predetermined level above that which is established in the fluid storage section 12 for the reasons described in connection with the pumping mechanism 30 of FIG. 1. As the limiting pressure is reached the fluid outside of the pumping mechanism will flow back into the fluid storage section 12 during the intervals between each of the successive manipulations of the fingers.

The fluid storage section 12 has two hollow diverging tails 16, 17 that are connected at their common end to the pumping mechanism by means of a flexible expansion and contraction bellows 20. A soft, but solid extension 21 forms one side of a chamber, or distal expansile section 22. The other side of the expansile section 22 is provided by means of a flexible outer membrane 23, this outer membrane covering the entire device, thereby rendering the device one single, integral unit. Thus, as shown, the expansile section 22 is in fluid communication with the pumping mechanism.

In operation and, as best shown in FIG. 3, the thumb and index fingers press in the direction of arrows 24, 25, respectively. This finger pressure expresses fluid within the pumping mechanism into the expansile section 22 in order to inflate the outer membrane 23 causing the penis (not shown) within which the prosthesis is implanted to swell and become rigid. As each charge of fluid is expressed into the expansile section 22, the loss of fluid from the storage section 12 is compensated through contraction of the bellows 20.

To prevent overdistention of the penis, however, as the fluid pressure within the expansile section 22 becomes too high relative to the pressure of the fluid remaining within the pumping mechanism, the higher pressure fluid in the expansile section flows back into the storage section 12. In this manner, an equilibrium is reached between the degree of inflation of the prosthesis and the pressure within the pumping mechanism and the storage section that is commensurate with the rigidity and swelling required for satisfactory sexual activity and a safe distention of the penis.

To restore the penis to a flaccid condition, the penis should be gently squeezed to press the fluid in the expansile section 22 back into the storage section 12. The bellows 20, during flaccid condition restoration, expands to accommodate the increased volume of fluid entrapped in the storage section 12.

As hereinbefore mentioned, to implant the conjoined single prosthesis within a body, an incision is made in the tunica albuginea (now shown) and the intercrural septum is divided. The prosthesis is then inserted into the penis with the end of the outer membrane 23 and the soft, solid extension 21 that are opposite to the pumping mechanism oriented toward the glans penis. In this circumstance, the prosthesis terminates distal to the corona of the glans penis. As best shown in FIG. 2, the two diverging tails 16, 17 are surgically lodged in separate ischial cavernosa, under the pubic arch.

Thus there is provided in accordance with the invention an inexpensive, reliable and relatively easy to implant apparatus for rendering selectively rigid the penis of an otherwise impotent man. Clearly, the cosmetic appearance of this selectively inflatable apparatus is superior to a number of available devices, is less expensive than other inflatable prosthetic devices, requires less hospitalization and is less expensive for the patient.

I claim:

1. An inflatable prosthetic device for implantation within a penis; the device comprising in combination:
 a fluid storage section;
 a pumping mechanism integral with and in fluid communication through at least one conduit formed therebetween with said fluid storage section;
 at least one membrane enclosing said pumping mechanism and said fluid storage section to form a distal expansile section that is in selective fluid communication with said pumping mechanism;
 a pressure relief valve for establishing fluid communication between said distal expansile section and said fluid storage section to establish a predetermined maximum fluid pressure within said distal section; and
 a distal stiffener integral with said pumping mechanism and protruding distally therefrom within said membrane in order to form said distal expansible section therebetween.

2. An inflatable device according to claim 1 further comprising a bellows interposed between said pumping mechanism and said fluid storage section to contract and thereby to compensate for fluid transferred from said storage section to said distal expansile section to render said expansile section rigid.

3. An inflatable device according to claim 1 wherein said fluid storage section further comprises a pair of diverging tails, said tails both being joined to said bellows.

* * * * *